(12) United States Patent
Jayaraman et al.

(10) Patent No.: US 9,170,165 B2
(45) Date of Patent: Oct. 27, 2015

(54) WORKFUNCTION MODULATION-BASED SENSOR TO MEASURE PRESSURE AND TEMPERATURE

(71) Applicant: International Business Machines Corporation, Armonk, NY (US)

(72) Inventors: Balaji Jayaraman, Bangalore (IN); Kota V. R. M. Murali, Bangalore (IN); Edward J. Nowak, Essex Junction, VT (US); Ninad D. Sathaye, Pune (IN); Rajesh Sathiyanarayanan, Chennai (IN)

(73) Assignee: GLOBALFOUNDRIES U.S. 2 LLC, Hopewell Junction, NY (US)

( * ) Notice: Subject to any disclaimer, the term of this patent is extended or adjusted under 35 U.S.C. 154(b) by 312 days.

(21) Appl. No.: 13/849,565

(22) Filed: Mar. 25, 2013

(65) Prior Publication Data
US 2014/0283616 A1  Sep. 25, 2014

(51) Int. Cl.
| | |
|---|---|
| *G01N 7/00* | (2006.01) |
| *G01L 9/00* | (2006.01) |
| *G01K 7/01* | (2006.01) |
| *G01N 27/414* | (2006.01) |
| *G01N 27/00* | (2006.01) |

(52) U.S. Cl.
CPC ............. *G01L 9/0042* (2013.01); *G01K 7/015* (2013.01); *G01N 27/4141* (2013.01); *G01N 27/002* (2013.01)

(58) Field of Classification Search
CPC .... G01K 11/003; G01K 7/015; G01L 9/0042; G01N 27/4141; G01N 27/002

USPC .......... 257/253, 467, 254, 414, 415; 374/178; 73/31.06, 23.2; 204/430–431
See application file for complete search history.

(56) References Cited

U.S. PATENT DOCUMENTS

| | | | |
|---|---|---|---|
| 4,042,946 A * | 8/1977 | Sokoloski | ..................... 257/253 |
| 5,670,718 A | 9/1997 | Nagahara | |
| 6,067,062 A | 5/2000 | Takasu et al. | |
| 6,218,687 B1 | 4/2001 | Ziegler | |
| 7,110,238 B1 * | 9/2006 | Xu et al. | ....................... 361/220 |

(Continued)

OTHER PUBLICATIONS

Aracil et al., "Pneumatic Free Piston Fabricated in SU-8 for MEMS Applications", 978-1-4244-7865-1/11©2011 IEEE, Proceedings of the 8th Spanish Conference on Electron Devices, CDE'2011.

(Continued)

*Primary Examiner* — Lisa Caputo
*Assistant Examiner* — Jonathan Dunlap
(74) *Attorney, Agent, or Firm* — Michael LeStrange; Roberts Mlotkowski Sarfran & Cole, P.C.

(57) ABSTRACT

A workfunction modulation-based sensor comprising a field-effect transistor (FET). The FET comprises a substrate, a gate dielectric, a metal gate, a source, a drain, and a layer of sensing material that is electrically connected to the metal gate. An electrical connection that connects to the source of the FET. An electrical connection that connects to the drain of the FET. An electrical connection that connects to the layer of sensing material. An environment that includes an adsorbate gas surrounding, at least a portion of, the layer of sensing material. Wherein the sensing material is adapted to adsorb, at least in part, the adsorbate gas. The amount of adsorbate gas adsorbed on the layer of sensing material modulates the workfunction of the FET such that the degree of adsorbate gas adsorption corresponds to one of the temperature or pressure associated with the environment of the FET.

20 Claims, 4 Drawing Sheets

(56) References Cited

U.S. PATENT DOCUMENTS

| | | | |
|---|---|---|---|
| 7,176,508 | B2 | 2/2007 | Joshi et al. |
| 7,278,322 | B1 | 10/2007 | Lantz |
| 7,459,732 | B2 * | 12/2008 | Fleischer et al. ............. 257/226 |
| 7,824,099 | B2 | 11/2010 | He et al. |
| 7,862,233 | B2 | 1/2011 | Hyde et al. |
| 7,918,123 | B2 | 4/2011 | Wilbertz et al. |
| 8,007,169 | B2 | 8/2011 | Opitz et al. |
| 8,152,363 | B2 * | 4/2012 | Nagahisa ........................ 374/1 |
| 8,754,454 | B2 * | 6/2014 | Bryant et al. ................ 257/253 |
| 8,866,505 | B2 * | 10/2014 | Baikie ...................... 324/754.01 |
| 8,899,098 | B2 * | 12/2014 | Senft et al. .................. 73/31.06 |
| 2005/0062116 | A1 * | 3/2005 | Edinger et al. ............... 257/414 |
| 2006/0174692 | A1 * | 8/2006 | Bonne et al. .................. 73/23.2 |
| 2008/0134759 | A1 * | 6/2008 | Mohammed-Brahim et al. ........................ 73/31.06 |
| 2010/0038725 | A1 * | 2/2010 | Chudzik et al. ............. 257/392 |
| 2011/0031986 | A1 * | 2/2011 | Bhat et al. .................... 324/686 |
| 2012/0090381 | A1 * | 4/2012 | Andersson ................. 73/31.06 |
| 2012/0171775 | A1 * | 7/2012 | Vogt et al. .................... 436/151 |
| 2013/0186178 | A1 * | 7/2013 | Usagawa ..................... 73/31.06 |

OTHER PUBLICATIONS

Bergveld et al., "Theory and application of the material work function for chemical sensors based on the field effect principle", 0957-0233/98/111801+08 © 1998 IOP Publishing Ltd., Netherlands, Aug. 21, 1998. Meas. Sci. Technol. 9 (1998) pp. 1801-1808.

Butefisch et al., "Novel micro-pneumatic actuator for MEMS", Sensors and Actuators A 97-98 (2002) 638-645, Nov. 22, 2001, © 2002 Elsevier Science, <www.elsevier.com/locate/sna>.

Dai et al., "Micro FET pressure sensor manufactured using CMOS-MEMS technique", Microelectronics Journal 39 (2008) pp. 744-749, Copyright 2007 Elsevier Ltd. doi: 10.1016/j.mejo.2007.12.015.

De Volder et al., "Microsized Piston-Cylinder Pneumatic and Hydraulic Actuators Fabricated by Lithography", Journal of Microelectromechanical Systems, vol. 18, No. 5, Oct. 2009, © 2009 IEEE.

Kolaczkiewicz et al., "Temperature Dependence of the Work Function of Adsorbate-Covered Metal Surfaces: A New Method for the Study of Two-Dimensional Phase Transitions", Jul. 30, 1984, pp. 485-488, vol. 53, No. 5, © 1984 The American Physical Society.

Sakurano et al., "Operation of a Work Function Type SOI Temperature Sensor up to 250 C"2007 IEEE International SOI Conference Proceedings, pp. 149-150, © 2007 IEEE.

Santagata et al., "A Novel 3-D Tube-Shaped Buried Poly-Si Pirani Gauge for Extended Dynamic Range With Small Footprint", © 2010 IEEE, pp. 643-646.

Santagata et al., "A Tube-Shaped Buried Pirani Gauge for Low Detection Limit With Small Footprint", Journal of Microelectromechanical Systems, vol. 20, No. 3, Jun. 2011, © 2010 IEEE, pp. 676-684, doi:10.1109/JMEMS.2011.2127457.

* cited by examiner

WORKFUNCTION MODULATION-BASED SENSOR TO MEASURE PRESSURE AND TEMPERATURE

FIELD OF THE INVENTION

The present invention relates generally to the field of sensors, and more particularly to workfunction based sensors to measure pressure and temperature.

BACKGROUND OF THE INVENTION

High-powered very large scale integration (VLSI) circuits are widely used in the electronics industry. Major uses of VLSI circuits include clock buffers, wordline drivers, and I/O buffers. Generally, VLSI circuits are comprised of a plurality of field effect transistors (FETs) laid out on a substrate. As transistors have decreased in size, the thickness of the silicon dioxide gate dielectric has steadily decreased to increase the gate capacitance and thereby drive current, raising device performance. However, as thickness has scaled below 2 nanometers, leakage currents due to tunneling have increased, which in turn have lead to higher power consumption and reduced device reliability. During their operation, VLSI circuits generate heat internally. This self-heating increases the junction temperature in the device, and can result in failure of the VLSI circuit.

In general, gates made using high-κ materials allow for increased gate capacitance with reduced associated leakage effects. The term high-K dielectric generally refers to a material with a high dielectric constant κ (as compared to silicon dioxide). High-κ dielectrics are used in semiconductor manufacturing processes where they are usually used to replace a silicon dioxide gate dielectric or another dielectric layer of a device. Some materials which have received considerable attention as high k gate materials are oxynitride (a silicon oxide dielectric that has been infused with a small amount of nitrogen), hafnium silicate, zirconium silicate, hafnium dioxide and zirconium dioxide.

Pressure sensors can be used to measure pressure variations in air as well as any other gas. The pressure variations in a sample gas are often measured against known values. These pressure variations can be an important parameter in determining various properties of a given gas sample. Pressure sensors that measure such pressure variations find widespread application in areas such as industrial process control, automobile engine monitoring and various biomedical processes. Such sensors would typically require high mechanical stability. Further, the sensors should have a good sensitivity and resolution to respective variations in pressure and temperature.

SUMMARY

Exemplary embodiments of the present invention provide a workfunction modulation-based sensor, and method of using the same, to determine the pressure and the temperature of an environment of the workfunction modulation-based sensor. Exemplary embodiments of the workfunction modulation-based sensor comprise a field-effect transistor (FET). The FET comprises a substrate, a gate dielectric, a metal gate, a source, a drain, and a layer of sensing material that is electrically connected to the metal gate. An electrical connection that connects to the source of the FET. An electrical connection that connects to the drain of the FET. An electrical connection that connects to the layer of sensing material. An environment that includes an adsorbate gas surrounding, at least a portion of, the layer of sensing material. Wherein the sensing material is adapted to adsorb, at least in part, the adsorbate gas. The amount of adsorbate gas adsorbed on the layer of sensing material modulates the workfunction of the FET such that the degree of adsorbate gas adsorption corresponds to one of the temperature or pressure associated with the environment of the FET.

DETAILED DESCRIPTION

Two commonly used types of silicon-based pressure sensors are piezoresistive and capacitive pressure sensors. Both the piezoresistive and capacitive pressure sensor uses a thin silicon diaphragm, which is fabricated by anisotropic etching of a thicker silicon substrate. In the piezoresistive pressure sensor, pressure variations in one side of the diaphragm results in a flexure, which is directly proportional to the applied pressure. The piezoresistive type of pressure sensor relies on stress-induced changes in the resistivity of diffused resistors in the diaphragm. The capacitive sensor relies on capacitive variations between the diaphragm and a metal plate, which is placed parallel and close to the diaphragm. Further, both types of the pressure sensors require the silicon chip attached to the metal plate to hermetically seal the chamber on one side of the diaphragm. However, the requirement of hermetic sealing increases the cost of the pressure sensor as the sealing is performed on an individual chip rather than on a complete wafer level.

In known art, FETs with varying degrees of impurities in the respective gate electrodes have been used to create temperature sensors. In general, two FETs with different respective work functions are used. The work function difference between the two FETs is substantially close to the band gap energy of the silicon substrate and can be used to calculate temperature. However, such sensors are limited in that they cannot be used to determine pressure.

Because of their manufacturing process, the aforementioned conventional thermal sensors exhibit a high susceptibility to drift. Therefore the aforementioned conventional thermal sensors have the disadvantage that they must be laboriously stabilized, since the changes in material properties over the service life bring about a drift of the sensor element. Even with such stabilization (e.g., tempering processes), this drift can in some cases still be enormous.

In solid-state physics, the workfunction (sometimes spelled work function) is the minimum energy (usually measured in electronvolts) needed to remove an electron from a solid to a point immediately outside the solid surface (or energy needed to move an electron from the Fermi level into vacuum). Here "immediately" means that the final electron position is far from the surface on the atomic scale but still close to the solid on the macroscopic scale. The workfunction is a characteristic property for any solid phase of a substance with a conduction band (whether empty or partly filled). In the context of a FET, the workfunction is herein to denote the effective workfunction of the FET.

For a metal, the Fermi level is inside the conduction band, indicating that the conduction band is partly filled. For an insulator, the Fermi level lies within the band gap, indicating an empty conduction band. In general, the minimum energy needed to remove an electron is about the sum of half the band gap and the electron affinity.

The present invention will now be described in detail with reference to the Figures. It should be noted that elements included in the figures are not drawn to scale.

In some exemplary embodiments a field-effect transistor (FET) sensor is exposed to the environment, i.e., the FET sensor is not enclosed. In such embodiments, an adsorbate gas is included in the environment of the FET. A FET sensor that is exposed to the environment is herein referred to as a bare FET sensor. Bare FET sensors are, in general, limited to measuring changes in pressure and not temperature. Bare FET sensors can be used to measure very low pressures in, for example, high vacuum environments.

Figure 3:
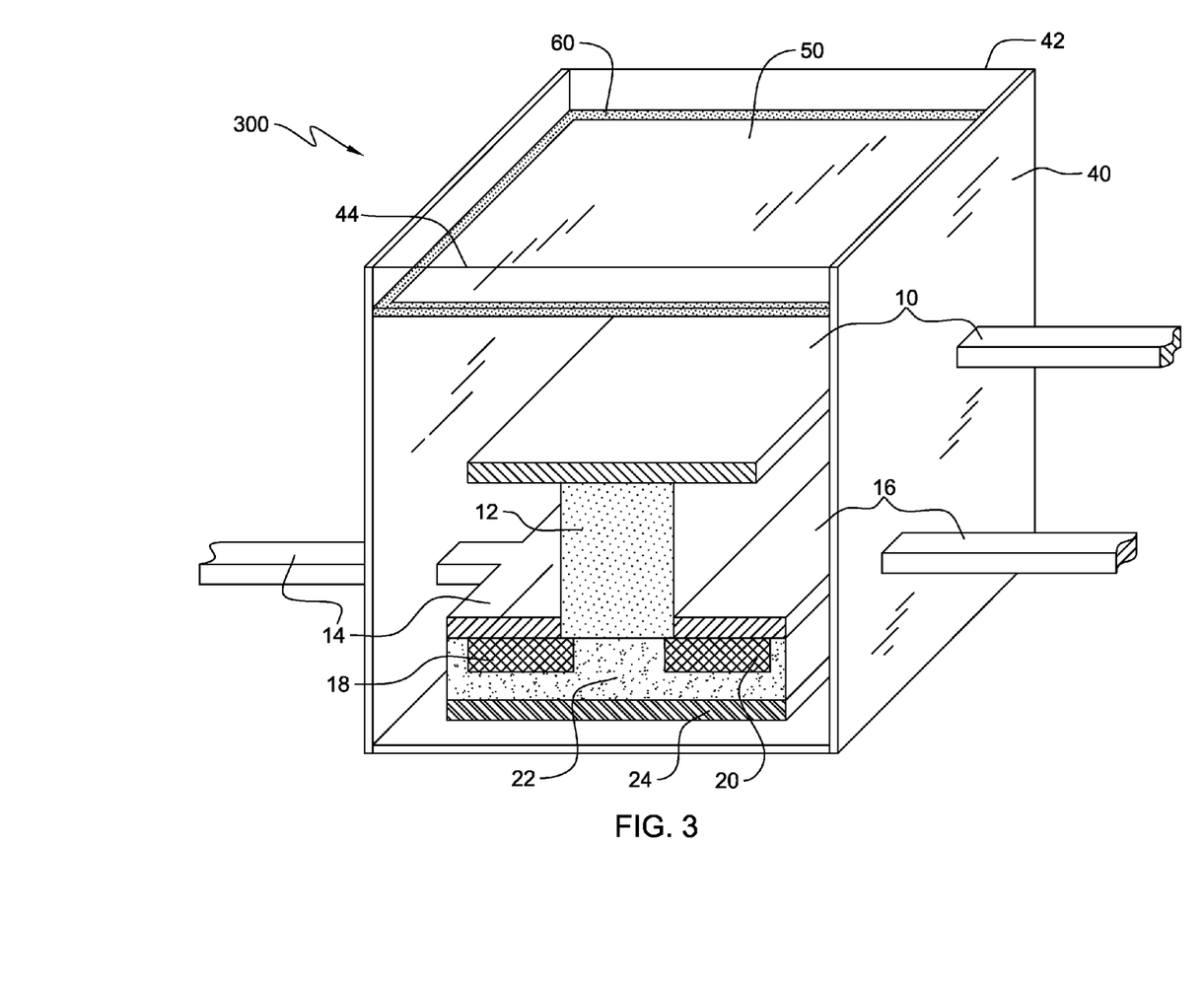
FIG. 3 is an illustration of an enclosed FET sensor configured to determine pressure, with movable wall positioned near the top of the chamber, in accordance with an exemplary embodiment.
Figure 4:
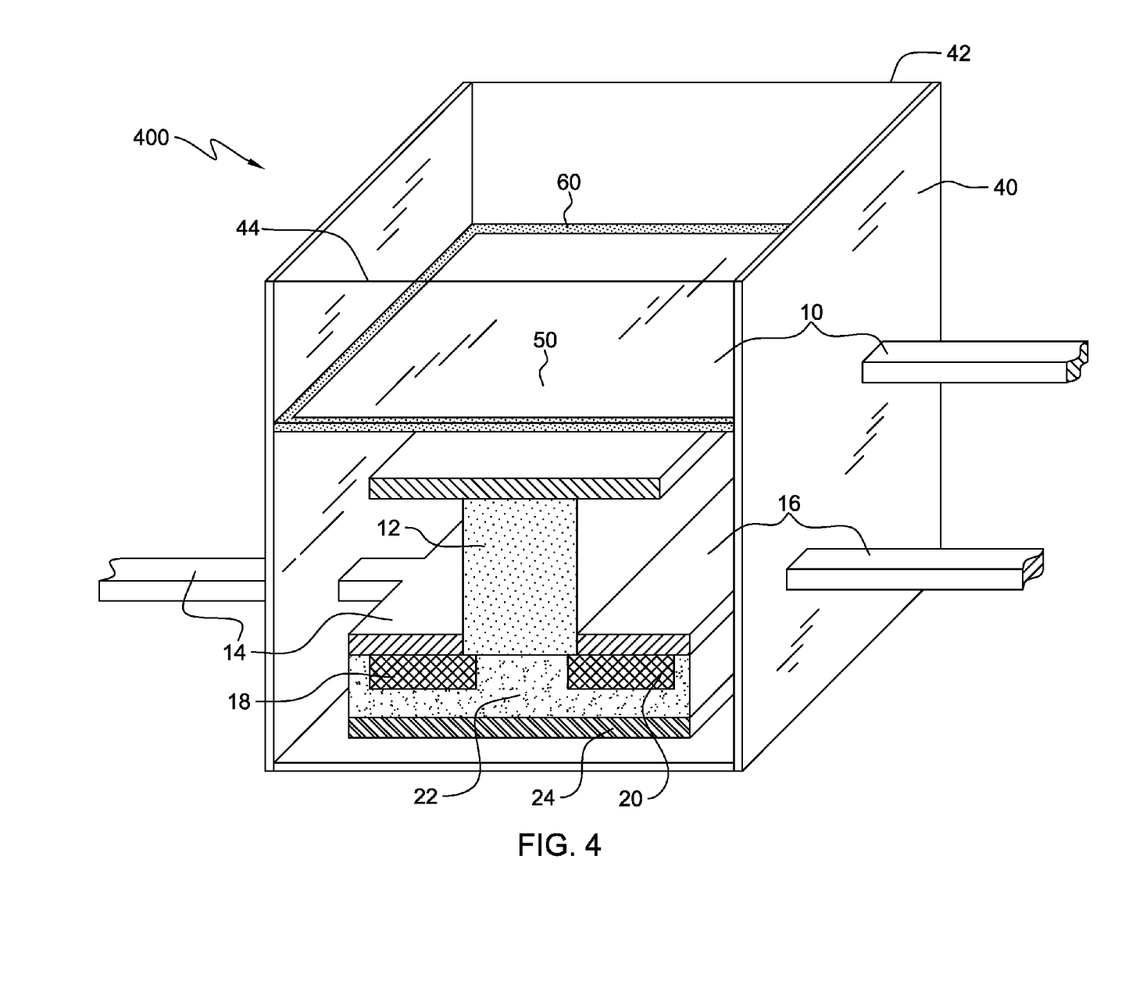
FIG. 4 is an illustration of an enclosed FET sensor configured to determine pressure, with movable wall positioned near sensing material, in accordance with an exemplary embodiment.

In other exemplary embodiments, a FET sensor is surrounded by an adsorbate gas filled chamber to form an enclosed FET sensor (see discussion of FIGS. 2, 3 and 4 below for further details). The adsorbate gas filled chamber constitutes a closed system. In other words there is no exchange of matter, specifically the adsorbate gas, between the chamber and the environment outside the chamber. For example, a bare FET can be enclosed by a vacuum chamber. As the adsorbate gas adsorbs onto the FET the workfunction of the FET changes, thereby changing the degree of current that can flow through the FET. In general, an enclosed FET sensor can be configured to measure changes in either temperature or pressure.

Figure 1:
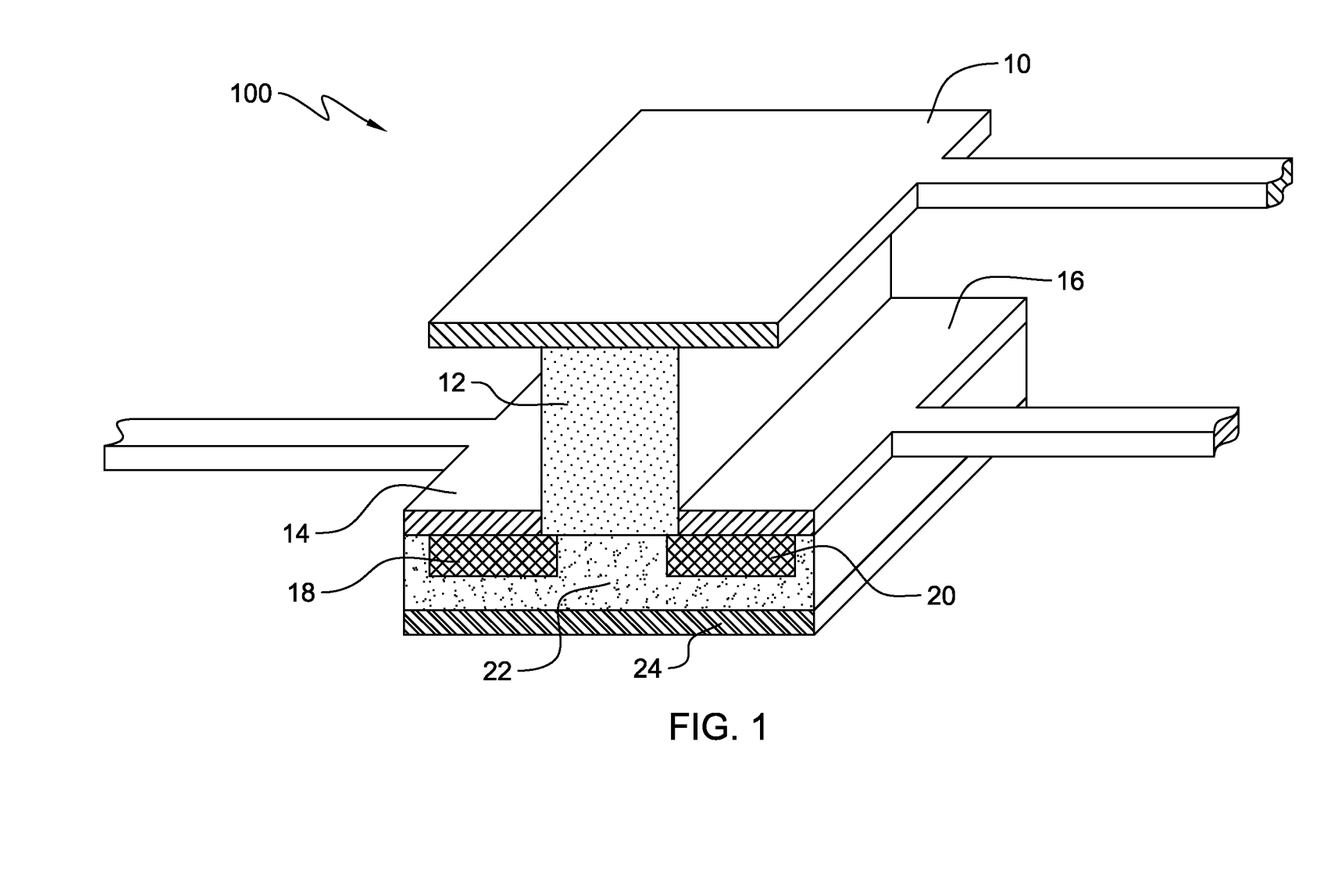
FIG. 1 is an illustration of a bare FET sensor, in accordance with an exemplary embodiment.

FIG. 1 is a diagram illustrating bare FET sensor 100. Bare FET sensor 100 is a FET that has been modified to include a sensing material 10, which is attached to gate 12. Bare FET sensor 100 further includes source 18, drain 20, source contact 14, drain contact 16, body 22, and substrate 24. In this embodiment, gate 12 is composed primarily of one or both of a high-k material and silicon dioxide (a gate dielectric material). In other embodiments, gate 12 includes other known alternative dielectric materials.

In general, FETs are majority-charge-carrier devices. Body 22, of bare FET sensor 100, includes a channel region (not depicted) through which the majority charge carriers, electrons or holes, flow from the source to the drain. In general, the channel is herein defined as the region of body 22, separating source 18 and drain 20, through which the majority of charge carriers flow. The conductivity of the channel is a function of potential applied across the gate and source terminals. Typically, source and drain terminal conductors of a FET are connected to the semiconductor through ohmic contacts. An ohmic contact is herein defined as a non-rectifying junction, i.e., a region in a semiconductor device that has been prepared so that the current-voltage (I-V) curve of the region is substantially linear and symmetric.

There are three main terminals, i.e., electrical connections, included in bare FET sensor 100. The terminals are source 18, drain 20, and gate 12 and sensing material 10. Source 18 is the terminal through which the majority carriers enter the channel. Drain 20 is the terminal through which the majority carriers leave the channel. Gate 12 and sensing material 10 together comprise the terminal that modulates the channel conductivity, i.e., through the application of voltage to sensing material 10, the current flowing out of drain 20 can be controlled.

Sensing material 10 is in electrical contact with gate 12. Sensing material 10 is a layer of adsorbent material that can adsorb adsorbate gas atoms/molecules to induce a shift in the workfunction of bare FET sensor 100. There are a number of materials with various degrees of surface area, realized through nano-patterning techniques, that can be used as sensing material 10. Typically, an adsorbate gas is chosen to match to a given sensing material. Conversely, a sensing material can be chosen to match an adsorbate gas in the environment of the FET sensor, e.g., as in the case of a bare FET sensor. In general, the more adsorbate gas adsorbed on sensing material 10 the higher the workfunction of the FET is shifted.

In exemplary embodiments, the ambient pressure/temperature surrounding the FET sensor determines the surface coverage (adsorbance) of the adsorbate gas on the sensing layer (sensing material 10) of the FET sensor. The surface coverage in turn uniquely determines the workfunction (WF) of the FET. The WF of the FET in turn relates to the threshold voltage of the FET, which may herein be referred to as $V_t$. As adsorbate gas adsorbs on the sensing layer, the $V_t$ of the FET is modified/shifted by a corresponding degree. As $V_t$ is decreased, the amount of current flowing through the FET increases proportionately and this current can be measured. Since the amount current flowing through the FET is regulated by the threshold voltage, either the current flowing through the FET or the threshold voltage can be used to calculate the ambient pressure or temperature of the adsorbate gas.

In general, the threshold voltage of a FET is usually defined as the gate voltage where an inversion layer forms at the interface between the insulating layer and the substrate of the transistor. The formation of the inversion layer allows the flow of majority carriers, electrons or holes, through the gate-source junction, e.g., through the channel of the FET. If the gate voltage is below the threshold voltage, then the transistor is turned off and, ideally, there is no current flowing from the drain to the source of the transistor. However, there is usually a small current flowing from the drain to the source of the transistor even for gate biases below threshold voltage. This small current varies exponentially with gate bias and is known as sub-threshold leakage. If the gate voltage is above the threshold voltage, then the transistor is turned on, due to there being many charge carriers in the channel. The presence of many charge carriers creates a low-resistance channel allowing a current to flow in the channel of the FET, e.g., from drain to source or vice versa.

In exemplary embodiments, an adsorption isobar is a function that relates the fractional amount of atoms adsorbed on the adsorbent layer to a temperature (T) measured at constant pressure. For adsorbate-adsorbent systems, the surface coverage ($\theta$) usually depends on several factors, such as concentration, pressure and temperature (T). For a closed system (no exchange of particles with atmosphere), $\theta$ depends only on temperature, wherein $\theta=f(T)$. Ab initio calculations show that the WF of a material changes with the surface coverage of adsorbate atoms. When such a material is combined with the gate stack of a FET, a WF shift will result in a change in $V_t$ of the device. Thus, $V_t=g(\theta)=g(f(T))$. Therefore, by measuring $V_t$, the average temperature of the adsorbate gas inside the closed system can be determined. A similar approach may be applied to determine the pressure of the adsorbate gas inside a closed system.

In exemplary embodiments, an adsorption isotherm (e.g., Langmuir isotherm, Fowler-Frumkin Isotherm, and Freundlich isotherm) relates the surface coverage (θ) of adsorbed atoms to pressure (P) at a constant temperature. For an isothermal closed system, θ depends only on pressure, i.e., θ=f (P) which yields an adsorption isotherm. Ab initio calculations have shown that a WF of a given material changes with the surface coverage of adsorbate atoms. When such a material is combined with the gate stack of a FET, a WF shift will result in a change in $V_t$ of the device. Hence, the equation $V_t = g(\theta) = g(f(P))$ can be derived. Therefore, by measuring $V_t$, we can compute P using the equation $P = f^{-1}(g^{-1}(V_t))$.

In exemplary embodiments, bare FET sensor 100 is not enclosed in a chamber, i.e., is directly exposed to the environment to be probed. In general, the environment of a bare FET sensor 100 is of a fixed volume, such as that of a high vacuum chamber. In general, a chamber, herein refers to a structure that encloses a bare FET sensor, isolating the bare FET sensor from the environment to be probed such that the matter included in the chamber can not be exchanged with the matter of the environment to be probed. For further details regarding chambers, see the discussion of FIGS. 2, 3, and 4.

In general, to calculate the pressure of the environment surrounding bare FET sensor 100, which is typically very low, the temperature of that environment must be known. As such, as the pressure of the environment varies, the amount of adsorbate gas that adsorbs on sensing material 10 varies respectively. Using the temperature of the environment to select an appropriate adsorption isotherm, an appropriate calculation can be made to determine the pressure based on the amount of adsorbate gas that is adsorbed on sensing material 10.

In alternative embodiments, a known range of temperatures of the environment can be used to generate a composite adsorption isotherm, e.g., an average adsorption isotherm. Such a composite adsorption isotherm can allow the amount of adsorbate gas that is adsorbed on sensing material 10 to be used to determine the pressure of the environment without knowing the temperature. However, a composite adsorption isotherm can produce a less accurate determination of pressure depending on both the range of temperatures used to create the composite adsorption isotherm and the actual temperature of the environment. For example, if the temperature of the environment is lower than the range of temperatures used to create the composite adsorption isotherm, then the calculated pressure will not correlate to the actual pressure of the environment.

In exemplary embodiments, a closed system consists of a FET sensor and an adsorbate gas enclosed in a chamber, wherein the pressure/temperature inside the chamber determines the surface coverage of the adsorbate gas on the sensing material. In various embodiments of the present invention, the chamber surrounding the FET sensor can have a fixed volume or a variable volume. A fixed volume chamber is needed to determine a temperature based on the amount of adsorbed adsorbate gas. A variable volume chamber is needed to determine an external environment pressure based on the amount of adsorbed adsorbate gas.

Figure 2:
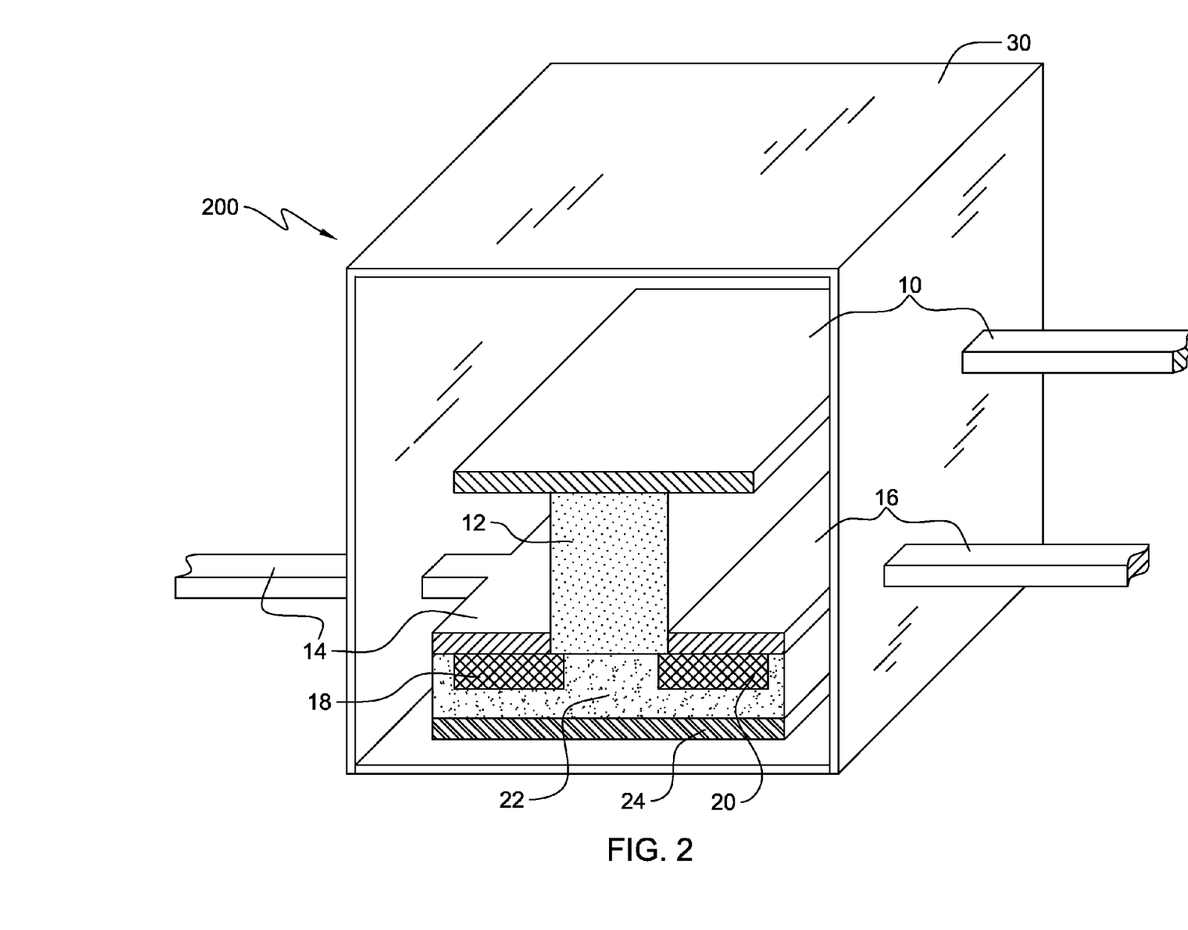
FIG. 2 is an illustration of an enclosed FET sensor that is configured to determine the temperature of the adsorbate gas in the chamber, in accordance with an exemplary embodiment.

In this embodiment, FIG. 2 is a diagram illustrating an enclosed FET sensor 200 that is configured to determine the temperature of the adsorbate gas in the chamber. In general an enclosed FET sensor 200 is created by enclosing a bare FET sensor 100 in a fixed volume adsorbate gas filled chamber 30. To aid in visualization, in FIG. 2, the front and rear walls of fixed volume adsorbate gas filled chamber 30 are not shown, but still exist. In general, as the temperature of the adsorbate gas rises, the amount of adsorbate gas which is adsorbed onto sensing material 10 changes. A change in adsorbance of the adsorbate gas results in a change in the current flowing through enclosed FET sensor 200. Thus, the amount of flowing current can be measured and used to determine the temperature of the adsorbate gas, and hence the temperature of the external environment can be determined.

In general, the average temperature of the adsorbate gas is equivalent to that of the environment outside of the chamber. As heat is transferred into and out of the adsorbate gas filled chamber, through the walls of the chamber, the temperature of the adsorbate gas changes to reflect the temperature of the external environment. Therefore, changes in the temperature of the external environment are reflected as changes in the average temperature of the adsorbate gas. However, as the transfer of heat into or out of the adsorbate gas is not instantaneous, there is a period of time where the temperature of the adsorbate gas is not equivalent to the external environment. It is therefore necessary to allow for an equilibration period, i.e., a period of time to allow the heat to transfer, before $V_t$ and current flowing through enclosed FET 200 sensor can be determined.

To simplify the description, FIG. 3 and FIG. 4 will be discussed concurrently. In this exemplary embodiment, FIG. 3 and FIG. 4 are diagrams illustrating FET sensors that are configured to determine the pressure of the adsorbate gas in the chamber. In general an enclosed FET sensor 300/400 is created by enclosing a bare FET sensor 100 in a variable volume adsorbate gas filled chamber 40. Since a relatively stable chamber temperature is required to make an accurate pressure determination, variable volume adsorbate gas filled chamber 40 further includes a thermostat, as well as heating and cooling elements to keep the temperature of the adsorbate gas relatively stable. To simplify FIGS. 3 and 4, the respective thermostats, heating and cooling elements are not depicted.

In this exemplary embodiment, the variable volume adsorbate gas filled chamber 40 includes a movable wall 50. In both FIGS. 3 and 4, for visualization purposes, the front and rear non-moving walls are not shown, but do exist. The location of the top edge of the front and rear non-moving walls are indicated by lines 44 and 42 respectively. To clarify, in this exemplary embodiment, there is only one moving wall, namely movable wall 50, which comprises the top wall of the chamber. In alternative embodiments, there may be multiple moving walls i.e., one or more walls, which can move and thereby alter the volume of the gas filled chamber.

In this embodiment, in general, the range of measurable pressures depends on the volume limitations of the chamber, the quantity of adsorbate gas in the chamber, and the temperature of the adsorbate gas. FIG. 3 illustrates an enclosed FET sensor, 300, configured to determine pressure with movable wall 50 positioned near the top of the chamber. This indicates that the pressure of the external environment is near the lower end of the range of pressure that can be measured by enclosed FET sensor 300 at a given temperature. Conversely, FIG. 4 illustrates an enclosed FET sensor, 400, configured to determine pressure with movable wall 50 positioned near sensing material 10. This indicates that the pressure of the external environment is near the upper limit of the range of pressure that can be measured by enclosed FET sensor 400 at a given temperature.

In general, as movable wall 50 moves up and down, the volume of the chamber changes accordingly. Movable wall 50 includes a seal 60 to maintain the closed system, i.e., seal 60 prevents matter from entering or leaving the chamber. As pressure is exerted on movable wall 50, the wall moves up or down until the pressure of the adsorbate gas inside the chamber is in equilibrium with the pressure of the external environment. The increase or decrease in the pressure associated with the external environment can thus be related to a corresponding increase or decrease in the pressure of the adsorbate gas. Barring a phase change of the adsorbate gas, as the pressure increases, the more adsorbate gas is adsorbed onto sensing material 10. As pressure is reduced less adsorbate gas adsorbs onto sensing material 10. Thus, changes in adsorbance of the adsorbate gas results in changes in the amount of current flowing through FET sensor 300/400. The changes in flowing current can be measured and used to determine the pressure of the adsorbate gas, and hence the pressure of the external environment can be determined.

There can be a small difference between the adsorbate gas pressure and the pressure of the external environment, where the difference between the pressures is not sufficient to initiate movement of movable wall 50. However, such differences can be mitigated with the use of a seal 60 with a low coefficient of friction and/or through the use of an appropriate lubricant to minimize friction. In alternative embodiments a chamber with a variable volume can be created using an elastic material that can stretch and contract to accommodate the changing volume of the adsorbate gas.

In some alternative embodiments a compound FET sensor can be created using multiple FETs and/or mixtures of adsorbate gases. In general, each FET, of a compound FET sensor, can be customized to operate at a different range of temperatures or pressures. The respective currents of each FET, individually or combined, can be used for a temperature or pressure calculation. For example, a compound FET sensor includes two FET sensors, A and B, enclosed in a single fixed volume chamber. The chamber contains a mixture of adsorbate gases, C and D, which respectively adsorb onto FET sensors A and B. As the temperature increases, the amount of adsorbate gas C that adsorbs onto FET sensor A approaches the limit of adsorption and the adsorption of adsorbate gas C levels off. However, the amount of adsorbate gas D adsorbing onto FET sensor B can continue to increase until the limit of adsorbate gas D adsorption has been reached. Until the limit of adsorbate gas D adsorption has been reached, the compound FET sensor will continue to function. As can be seen in the previous example, the range of a compound FET sensor can be greater than a that of a single FET sensor.

In certain embodiments, the calculated temperature, pressure, or V, can be applied to and corrected using a calibration curve, whereby a more accurate determination of actual temperature and/or pressure of the external environment can be made. In yet other embodiments, the chamber can be converted from a fixed volume to a variable volume. Converting the chamber from a fixed volume to a variable volume allows one FET to determine changes in either pressure or temperature depending on the configuration of the chamber.

Some of the advantages of the proposed FET based sensor, in exemplary embodiments, can include a wide sensing range, and a high degree of sensitivity. In general, the proposed FET based sensors are not limited to any particular pressure range. Conversely, piezoresistive sensors are, typically, operable only at substantially larger pressures compared to the proposed FET based sensor. Further, in general, the FET based sensor, in exemplary embodiments, has a substantially smaller silicon footprint when compared to Pirani gauges, which are operable at very low pressures.

Having described the preferred embodiment of creating workfunction based sensors to measure pressure and temperature (which are intended to be illustrative and not limiting), it is noted that modifications and variations may be made by persons skilled in the art in light of the above teachings. As such, embodiments of the present invention may be used in a variety of electronic applications that include printed circuit boards and related structures.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While exemplary embodiments of the present invention have been described in detail in connection with only a limited number of embodiments, it should be readily understood that the exemplary embodiments of the present invention are not limited to such disclosed embodiments. Rather, exemplary embodiments of the present invention can be modified to incorporate any number of variations, alterations, substitutions or equivalent arrangements not heretofore described, but which are commensurate with the spirit and scope of the present invention. Additionally, while various exemplary embodiments of the present invention have been described, it is to be understood that aspects of the present invention may include only some of the described exemplary embodiments. Accordingly, exemplary embodiments of the present invention are not to be seen as limited by the foregoing description. A reference to an element in the singular is not intended to mean "one and only one" unless specifically stated, but rather "one or more." All structural and functional equivalents to the elements of the various exemplary embodiments described throughout this disclosure that are known or later come to be known to those of ordinary skill in the art are expressly incorporated herein by reference and intended to be encompassed by exemplary embodiments of the present invention. It is therefore to be understood that changes may be made in the particular embodiments disclosed which are within the scope of the present invention as outlined by the appended claims.

Each respective figure, in addition to illustrating the structure of the present invention at various stages and configurations, also illustrates the respective steps of the method for the fabrication/manufacture of workfunction based sensor to measure pressure and temperature.

What is claimed is:

1. A workfunction modulation-based sensor comprising:
a field-effect transistor (FET) comprising a substrate, a gate dielectric, a metal gate, a source, a drain, and a layer of sensing material provided on a top of the gate dielectric and that is electrically connected to the metal gate;
an electrical connection that connects to the source of the FET;
an electrical connection that connects to the drain of the FET;
an electrical connection that connects to the layer of sensing material; and
an environment that includes an adsorbate gas surrounding, at least a portion of, the layer of sensing material;
wherein the sensing material is adapted to adsorb, at least in part, the adsorbate gas, and the amount of adsorbate gas adsorbed on the layer of sensing material modulates the workfunction of the FET such that the degree of adsorbate gas adsorption corresponds to one of the temperature or pressure associated with the environment of the FET.

2. The workfunction modulation-based sensor of claim 1, the workfunction modulation-based sensor further includes a chamber that encloses the FET and the adsorbate gas.

3. The workfunction modulation-based sensor of claim 2, wherein at least a portion of, the electrical connection that connects to a source of the FET, the electrical connection that connects to a drain of the FET, or the electrical connection that connects to the layer of sensing material, respectively extends beyond the chamber.

4. The workfunction modulation-based sensor of claim 2, wherein the degree of adsorbate gas that is absorbed by the layer of sensing material corresponds to one of the temperature or pressure associated with an environment that is external to the chamber.

5. The workfunction modulation-based sensor of claim 4, wherein the chamber creates a n closed system such that there is no exchange of matter between the chamber and the environment exterior to the chamber.

6. The workfunction modulation-based sensor of claim 1, wherein the adsorbate gas induces a measurable shift in the workfunction and a threshold voltage of the workfunction modulation based sensor when the adsorbate gas is adsorbed on the layer of sensing material.

7. The workfunction modulation-based sensor of claim 1, wherein the layer of sensing material and adsorbate gas are chosen such that the magnitude of the work function-modulation is dependent on the adsorbate gas surface coverage ($\theta$) on the layer of sensing material.

8. The workfunction modulation-based sensor of claim 1, further including a thermostat.

9. The workfunction modulation-based sensor of claim 1, further including a heating element.

10. The workfunction modulation-based sensor of claim 1, further including a cooling element.

11. The workfunction modulation-based sensor of claim 1, wherein the gate dielectric is composed primarily of one or both of a high-k material and silicon dioxide.

12. A workfunction modulation-based sensor comprising:
a field-effect transistor (FET) comprising a substrate, a gate dielectric, a metal gate, a source, a drain, and a layer of sensing material that is electrically connected to the metal gate;
an electrical connection that connects to the source of the FET;
an electrical connection that connects to the drain of the FET;
an electrical connection that connects to the layer of sensing material;
an environment that includes an adsorbate gas surrounding, at least a portion of, the layer of sensing material;
wherein the sensing material is adapted to adsorb, at least in part, the adsorbate gas, and
the amount of adsorbate gas adsorbed on the layer of sensing material modulates the workfunction of the FET such that the degree of adsorbate gas adsorption corresponds to one of the temperature or pressure associated with the environment of the FET, and
a locking device to change the configuration of the chamber to a fixed volume configuration to determine a temperature of the environment of the FET or to a variable volume configuration to determine a pressure of the environment of the FET.

13. A method of determining pressure using a workfunction modulation-based sensor, the method comprising:
determining the current flowing through a workfunction modulation-based sensor;
determining, based on the flowing current, one or more of the threshold voltage, and the adsorbate gas surface coverage ($\theta$) on a layer of sensing material of the workfunction modulation-based sensor; and
determining the pressure of an environment of the workfunction modulation-based sensor based on one or more of the flowing current, the workfunction, threshold voltage, and the adsorbate gas surface coverage ($\theta$) on the sensing layer.

14. The method of claim 13, wherein determining the pressure of the environment of the workfunction modulation-based sensor based on one or more of the flowing current, the workfunction, threshold voltage, and the adsorbate gas surface coverage ($\theta$) on the sensing layer includes using one or more functions to calculate the pressure of the environment of the workfunction modulation-based sensor.

15. The method of claim 14, wherein the one or more functions, used to calculate the pressure of the environment of the workfunction modulation-based sensor, relate one or more of the adsorbate gas surface coverage ($\theta$) to an adsorption isotherm, the adsorbate gas surface coverage ($\theta$) to pressure, relate the workfunction to pressure, the flowing current to pressure, the voltage threshold to pressure, the voltage threshold to the workfunction, the voltage threshold to the current flowing, the voltage threshold to the pressure of the environment, the flowing current to the pressure of the environment, the workfunction to the pressure of the environment, and the adsorbate gas surface coverage ($\theta$) to the pressure of the environment.

16. The method of claim 13, wherein the environment of the workfunction modulation-based sensor comprises a variable volume chamber containing the adsorbate gas, wherein the temperature of the chamber and adsorbate gas are substantially stable, and wherein the pressure inside the chamber correlates to a pressure of an environment that is external to the chamber.

17. A method of determining temperature using a workfunction modulation-based sensor, the method comprising:
determining the current flowing through a workfunction modulation-based sensor,
wherein the workfunction modulation-based sensor is enclosed by a fixed volume chamber containing adsorbate gas;
determining, based on the flowing current, one or more of the threshold voltage, and the adsorbate gas surface coverage ($\theta$) on a layer of sensing material of the workfunction modulation-based sensor; and
determining the temperature of an environment of the workfunction modulation-based sensor based on one or more of the flowing current, the workfunction, threshold voltage, and the adsorbate gas surface coverage ($\theta$) on the sensing layer.

18. The method of claim 17, wherein determining the temperature of an environment of the workfunction modulation-based sensor based on one or more of the flowing current, the workfunction, threshold voltage, and the adsorbate gas surface coverage (8) on the sensing layer includes using one or more functions to calculate the temperature of the environment of the workfunction modulation-based sensor.

19. The method of claim 18, wherein the one or more functions, used to calculate the temperature of the environment of the workfunction modulation-based sensor, relate one or more of the adsorbate gas surface coverage ($\theta$) to an adsorption isobar, the adsorbate gas surface coverage (θ) to temperature, the workfunction to temperature, the flowing current to temperature, the voltage threshold to temperature, the voltage threshold to the workfunction, the voltage threshold to the current flowing, the voltage threshold to the temperature of the environment, the flowing current to the temperature of the environment, the workfunction to the temperature of the environment, and the adsorbate gas surface coverage (θ) to the temperature of the environment.

20. The method of claim 17, wherein the environment of the workfunction modulation-based sensor comprises a fixed volume chamber containing the adsorbate gas, wherein the pressure of the chamber and adsorbate gas are substantially stable, and wherein the temperature inside the chamber correlates to a temperature of an environment that is external to the chamber.

* * * * *